United States Patent [19]

Lasher

[11] 4,186,196

[45] Jan. 29, 1980

[54] TOPICAL ANTI-FUNGICIDE PREPARATION

[76] Inventor: Edward A. Lasher, 1141 Shadow Hill Way, Beverly Hills, Calif. 90210

[21] Appl. No.: 678,021

[22] Filed: Apr. 19, 1976

[51] Int. Cl.² .................... A61K 33/42; A61K 31/20
[52] U.S. Cl. .................................... 424/128; 424/318
[58] Field of Search ............................... 424/128, 318

[56] References Cited

PUBLICATIONS

The Merck Index Eighth Edition, (1968), p. 824.

The Dispensatory of the United States of America, 25th Edition, (1955), pp. 1051–1052.
Handbook of Non-Prescription Drugs, (1973 Edition), pp. 161–166, and 176–179.

*Primary Examiner*—Leonard Schenkman
*Attorney, Agent, or Firm*—Jay H. Quartz

[57] ABSTRACT

A formulation for the treatment of skin conditions, including fungus infections and psoriasis in humans, comprises undecylenic acid and phosphoric acid as the active constituents in specific amounts in a suitable solvent carrier.

6 Claims, No Drawings

TOPICAL ANTI-FUNGICIDE PREPARATION

BACKGROUND OF THE INVENTION

This invention relates to anti-fungus preparations and, more specifically, to topical preparations for the cure of fungus and other skin conditions in humans.

Many persons are afflicted with fungus infections such as those which grow under the nails. Such infections include the yeast type (Monilia) and mold type (Tinea Rubrum). At present, there is no effective preparation for the topical treatment of these fungus conditions. Therefore, treatment has been primarily by ingested preparations such as griseofulvin, which is an anti-fungal antibiotic. However, use of this preparation can result in serious side effects including gastro-intestinal disturbances. Furthermore, this method of treatment is not highly effective.

In addition to the aforementioned skin infections, many persons suffer from psoriasis for the treatment of which there are a number of topically-applied compounds. However, these compounds are of only limited effectiveness and they often exhibit undesirable side effects. For example, various sulphur compounds and steroid derivatives can produce serious side effects, whereas coal tar is rather odorous and only controls without curing. Psoriasis may also be treated internally with, for example, methotrexate. However, this material can also produce gastro-intestinal disorders as well as skin reactions.

In summary, there is a present need for medication which can be used effectively to treat the aforementioned skin-related disorders without attendant adverse side effects.

SUMMARY OF THE INVENTION

This invention is embodied in a topical preparation which comprises, as active constituents, undecylenic acid and phosphoric acid in specific weight ratios. A solvent for these active components is included in this preparation although the active ingredients may be prepared and sold separately from the solvent which can be added at the time when this preparation is to be used.

The preparation of this invention is applied to a person's fungus condition or other skin ailment periodically until the condition has cleared. The length of treatment is primarily determined by the length of time that a person has had the fungus condition since the latter tends to become denser with time and, therefore, more resistant to treatment.

This preparation has been used successfully to treat fungus under a person's nails which earlier did not respond to treatment using the heretobefore-described prior art treatment methods and compositions. Additionally, preliminary results indicate that it can be employed successfully in the treatment of psoriasis and moles.

DESCRIPTION OF THE PREFERRED EMBODIMENT

The herein-described topical preparation comprises, as active constituents, phosphoric acid and a mono-unsaturated, mono-carboxylic acid. Specifically, the latter acid is undecylenic acid. It is presently believed that the undecylenic acid improves the performance of the phosphoric acid and thereby is an active constituent. These active constituents are employed in combination with a solvent.

The phosphoric acid constituent may be present as orthophosphoric acid ($H_3PO_4$) or as other phosphorous-containing acid compounds which form orthophosphoric acid in the presence of water or air. Examples of such compounds include: metaphosphoric acid ($HPO_3$); pyrophosphoric acid ($H_4P_2O_7$); hypophosphoric acid ($H_4P_2O_6$); hypophosphorous acid ($H_3PO_2$) and phosphorous acid ($H_3PO_3$). If an acid of phosphorous other than orthophosphoric acid is employed, any water needed to change it to the ortho form can come from a person's skin but is preferably included in the topical preparation as part of the solvent. Because of its low cost with respect to anhydrous orthophosphoric acid, it is preferred to employ analytically pure orthophosphoric acid which is sold as an 85% (by weight) aqueous solution. As used hereinafter in this section for shorthand purposes, the term "phosphoric acid" means orthophosphoric acid and any of the aforementioned phosphorous-containing acids which form orthophosphoric acid in the presence of water or air.

The active constituents comprise between about 25% and about 75% by weight of the total weight of the solvent plus active constituents. Below about 25%, the concentration of the active constituents becomes too diluted. Above about 75%, the amount of solvent becomes insufficient to provide the decrease in the viscosity of the active constituents necessary to enable the herein-described preparation to penetrate into the small interstices in the skin-related conditions which are treatable with this preparation.

The phosphoric acid is employed in an amount between about 5% and about 85% by weight of the total weight of the active constituents with the undecylenic acid comprising the remainder. Below about 5%, the herein-described preparation becomes ineffective whereas, above about 85%, the phosphoric acid can injure healthy skin and cause it to peel. In general, the phosphoric acid concentration in a given preparation will be in the lower end of the aforementioned range for psoriasis or fungus conditions which are relatively new, whereas the phosphoric acid concentration will be in the upper end of that range for such conditions which have existed for a long time and which have had a chance to form thick, dense scales.

The solvent is one which prevents the undecylenic acid from separating from the phosphoric acid, particularly in the presence of water. Various organic solvents may be employed alone or in combination. Lower molecular weight alcohols, such as isopropyl alcohol and ethanol, are preferably employed as the solvent. Water, of course, may be included as part of the solvent. If water forms part of the solvent, it will comprise a minor portion of the total solvent with the organic fraction comprising the major portion.

The herein-described preparation may be applied topically by any convenient method as is well known. For fungus conditions under a person's nails, a very fine hypodermic needle may be employed to insert the preparation between the nail and underlying skin. Additionally, topical application includes the application of this preparation to fungus or scale which has existed for some time with resulting thickening by first disturbing the surface of the fungus or scale to expose underlying layers and then covering the latter with the preparation.

The invention will be further described by the following Examples.

EXAMPLE 1

A preparation having the following formula was made up with each of the identified components being present in the indicated amounts as a percentage of the total preparation weight: undecylenic acid—36.36%; orthophosphoric acid—19.23%; water—3.41%; and isopropyl alcohol—40.91%. This preparation was employed to treat a mold-type fungus infection of a person's fingernails which had existed for about two years and which had been resistant to treatment by prior art methods.

Sufficient solution was applied to the skin under each nail to lightly coat the exposed areas. This amounted to about 0.01 ml. per nail. A fine hypodermic needle was employed to apply the solution to the affected areas under the nails. This was done once/day for about four weeks. At the end of this period, the fungus condition was cured. About 0.03 to 0.04 ml. for all ten fingers was applied to the fingers every 3-4 days for about two months without change, that is, without return of the fungus.

EXAMPLE 2

An antifungus solution was made up consisting of 25.51% by weight undecylenic acid, 26.15% by weight orthophosphoric acid, 4.46% by weight water, and 43.88% by weight isopropanol.

This solution was employed to treat fungus condition of a person's toenails which had persisted for 30 years. About twice the amount of this solution was used in each daily treatment as was used in Example 1. Treatment was continued for two weeks with noticeable improvement.

EXAMPLE 3

A solution consisting of 34.15% by weight undecylenic acid, 25.0% orthophosphoric acid, 4.27% water, and 36.59% isopropanol was employed to treat psoriasis which had persisted for over forty years. Treatment was not on a daily basis. In spite of this, noticeable improvement was observed after only a few weeks.

EXAMPLE 4

The following solution was employed to remove a mole which was about 0.5 in. in diameter and about 0.190 in. thick: 5.85% by weight undecylenic acid, 27.28% hypophosphorous acid, 27.78% water, and 38.6% isopropanol. Only a single application of this solution was made to the mole. It was completely removed two weeks from this application.

I claim:
1. A topical preparation for the treatment of skin fungus infections and psoriasis, comprising:
   (a) undecylenic acid;
   (b) a phosphorous-containing acid which forms orthophosphoric acid in the presence of water or air; and
   (c) a solvent for said (a) and (b);
said (b) comprising between about 5% and about 85% by weight of the total weight of said (a) and (b), and said (a) and (b) comprising between about 25% and about 75% by weight of the total weight of said (a), (b) and (c).

2. The preparation of claim 1 wherein said solvent is a lower molecular weight alcohol selected from the group consisting of ethanol and isopropyl alcohol.

3. The preparation of claim 2 wherein said solvent includes water in a minor amount with respect to said alcohol such that said undecylenic and phosphorous-containing acids are maintained in solution.

4. An intermediate preparation for combination with a solvent for said intermediate preparation to provide a topical preparation comprising about 25% to about 75% by weight of said intermediate preparation for the treatment of skin fungus infections and psoriasis, said intermediate preparation comprising (a) undecylenic acid and (b) a phosphorous-containing acid which forms orthophosphoric acid in the presence of water or air, said (b) comprising between about 5% and about 85% by weight of the total weight of said (a) and (b).

5. The intermediate preparation of claim 4 wherein said phosphorous-containing acid is a material selected from the group consisting of: ortho- and metaphosphoric acid; pyrophosphoric acid; hypophosphoric acid; hypophosphorous acid; and phosphorous acid.

6. A topical preparation for the treatment of skin fungus infections and psoriasis, comprising:
   (a) undecylenic acid;
   (b) a phosphorous-containing acid member which is a material selected from the group consisting of ortho- and metaphosphoric acid, pyrophosphoric acid, hypophosphoric acid, hypophosphorous acid and phosphorous acid, said acid member comprising about 5% to about 85% by weight of the total weight of said (a) and (b); and
   (c) a solvent for said (a) and (b) consisting of a major portion of an organic solvent selected from the group consisting of ethanol and isopropyl alcohol and a minor portion of water, said (a) and (b) comprising between about 25% and about 75% by weight of the total weight of said (a), (b) and (c).

* * * * *